(12) United States Patent
Qin et al.

(10) Patent No.: US 8,158,845 B2
(45) Date of Patent: Apr. 17, 2012

(54) WOUND DRESSING

(75) Inventors: Yimin Qin, Northwich (GB); Denis Keith Gilding, Winsford (GB)

(73) Assignee: Advanced Medical Solutions Limited (GB)

( * ) Notice: Subject to any disclaimer, the term of this patent is extended or adjusted under 35 U.S.C. 154(b) by 0 days.

(21) Appl. No.: 11/167,915

(22) Filed: Jun. 27, 2005

(65) Prior Publication Data

US 2006/0067992 A1   Mar. 30, 2006

Related U.S. Application Data

(63) Continuation of application No. 10/884,929, filed on Jul. 6, 2004, now abandoned, which is a continuation of application No. 08/894,548, filed on Aug. 21, 1997, now abandoned.

(30) Foreign Application Priority Data

Oct. 27, 1994   (GB) .................................. 9421653.8

(51) Int. Cl.
*A61F 13/00*   (2006.01)

(52) U.S. Cl. ................ 602/48; 602/41; 602/42; 602/43; 602/44; 602/45; 424/449

(58) Field of Classification Search .......... 604/304–308; 602/41–59; 424/443–449
See application file for complete search history.

(56) References Cited

U.S. PATENT DOCUMENTS

| | | | | |
|---|---|---|---|---|
| 2,893,388 | A | * | 7/1959 | Ganz .............................. 602/43 |
| 4,513,739 | A | * | 4/1985 | Johns .............................. 602/52 |
| 5,052,381 | A | * | 10/1991 | Gilbert et al. ................... 602/52 |
| 5,674,524 | A | * | 10/1997 | Scherr .......................... 424/445 |
| 5,782,787 | A | * | 7/1998 | Webster ......................... 602/46 |
| 5,830,496 | A | * | 11/1998 | Freeman ....................... 424/445 |

OTHER PUBLICATIONS

Decision Issued in EP Application No, 95934759.2, dated Dec. 8, 2009.

\* cited by examiner

*Primary Examiner* — Kim M Lewis

(74) *Attorney, Agent, or Firm* — Woodard, Emhardt, Moriarty, McNett & Henry LLP

(57) ABSTRACT

A wound dressing comprises in combination (i) a first wound contact layer which preferably has a positive effect on the healing of the wound, and (ii) a second layer of greater hydrophilicity than the first layer.

4 Claims, No Drawings

WOUND DRESSING

This application claims priority to and is a continuation of application Ser. No. 10/884,929, filed Jul. 6, 2004 now abandoned which is a continuation of application Ser. No. 08/894,548, filed Aug. 21, 1997 now abandoned, which is hereby incorporated by reference.

The present invention relates to wound dressings.

For the treatment of many types of wounds, particularly medium to highly exuding wounds (e.g. 2nd and 3rd degree burns, decubitus ulcers and leg ulcers) it is necessary to ensure that bulk exudate is removed from the wound and peripheral skin to reduce or eliminate maceration. Prior art dressings have not always proved satisfactory in venting the large amount of exudate present in a wound. As such, the dressing becomes saturated and this results in maceration and excoriation. Additionally, the dressing may require to be changed relatively frequently and this is a labour intensive operation.

According to the present invention there is provided a wound dressing provided in combination
  (i) a first wound contact layer which preferably has a positive effect on the healing of the wound, and
  (ii) a second layer of greater hydrophilicity than the first layer.

Layer (i) is designed to provide a positive action in assisting healing of the wound and may take various forms (as described later) depending on the type of wound to be treated. The provision of layer (ii) (which is of greater hydrophilicity than layer (i) ensures that exudate present in layer (i) may pass into layer (ii) so as to increase the time before layer (i) becomes saturated. Preferably the hydrophilicity of layer (ii) is at least twice, and more preferably 3 to 5 times, that of layer (i).

Layer (i) (i.e. the wound contact layer) will generally be relatively thin (e.g. 50-1000 microns) and may be such as interact positively with the wound to assist healing thereof. Thus, for example, layer (i) may be one which provides for clotting via agglutination of red cells. Alternatively, the layer may be one which is capable of debriding the wound. A further possibility is for the layer to be one which delivers a component to the wound, e.g. an ion, drug, or anti-microbial agent. Examples of the materials which may be used for layer (i) are as follows:
  (a) calcium alginate which will provide calcium ions for haemostasis;
  (b) zinc alginate to deliver zinc ions into the wound to assist healing;
  (c) silver alginate to deliver silver ions as powerful anti-microbial agents to infected wounds;
  (d) chitosan to provide haemoglutination (i.e. clotting by gelation of red cells leaving the intrinsic and extrinsic clotting cascade intact). Chitosan also appears to have some beneficial effects on contact allergies and anti-microbial activity by stimulating the oxidative attack of white cells. Chitosan has also been reported to assist healing and reduce scarring;
  (e) pectin for stimulating autolysis and wound debridement. The pectin may be provided, for example, as pectin/carboxymethyl cellulose/alginate or pectin/alginate;
  (f) silver N,O-carboxymethyl chitosan or silver O-carboxymethyl chitosan;
  (g) a gauze material prepared as described in our earlier U.K. Patent Application No. 9415828 and incorporating silver ions for delivery to the wound;
  (h) a dehydrated hydrogel, e.g. of alginate or chitosan, which is of high integrity when it picks up water.

Layer (i) may be provided as a woven, non-woven or knitted material or as a gel. The layer may be in the form of a "rope" for deep cavities or an amorphous gel for sinuses.

Various species may be incorporated in layer (i) for delivery to the wound, e.g.
  simple anti microbial agents (e.g. $Zn^{2+}$ and $Ag^+$) and metal ions which are enzyme cofactors
  enzymes such as collogenase and metallo proteases such as plasmin or plasminogen which can be dosed into layer (i) to be released into the wound during healing to aid fibrinolysis and reduce scar formation
  drugs, such as anti-inflammatories etc., for dermatological application.

Layer (i) will also capture proteins and growth factors from the wound, initially by adsorption and as this layer hydrates later in the healing process these proteins and growth factors will be delivered back to the healing wound.

Layer (ii) is preferably also of a woven, non-woven or knitted fibrous material, e.g. a felt.

Layer (ii) will generally have a thickness of 1000 to 5000 microns, preferably 1000 to 2500 microns and may comprise
  (a) sodium alginate/calcium alginate felt (e.g. containing 20-60% sodium);
  (b) a sodium calcium carboxymethyl cellulose felt;
  (c) a sodium zinc carboxymethyl cellulose felt;
  (d) a sodium calcium polyacrylate felt; or
  (e) a sodium calcium carrageenin felt.
  (f) an alginate/CMC felt.
  (g) carboxymethyl cellulose (CMC) felt; or
  (h) N,O-carboxymethyl chitosan (NOCC) felt.

The sodium in the above materials may be replaced by potassium.

One particular example of wound dressing in accordance with the invention comprises chitosan as layer (i) and an alginate or alginate/CMC felt as layer (ii).

As explained above, layer (ii) is of greater hydrophilicity than layer (i). The requisite hydrophilicity (rate of exudate absorption) for layer (ii) may be obtained by mixing fibres of varying sodium/calcium ratios (for felts (a), (b), (d), and (e)) and by mixing fibres of varying sodium/zinc ratios (for felt (e)). The absolute capacity of the felt for absorbing exudate may be varied by mixing fibres of varying hydrophilicity. For example the absorption capacity of felts made from CMC, polyacrylate or NOCC, all of which are powerfully hydrophilic, may be lowered by the incorporation of alginate fibres. Alternatively, materials of the requisite absorption capability may comprise alginates co-spun with other polymeric materials as disclosed in our copending U.K. Patent Application No. 9419572.

As an alternative to layers (i) and (ii) both being non-woven, it is possible for layers (i) and/or (ii) to be of other types of material (provided that layer (ii) is more hydrophilic than layer (i)). Examples of such alternative constructions are as follows.

(1) Layer (i) is a non-woven felt and layer (ii) is a hydrogel. An example of such a dressing is one comprising a non-woven felt of chitosan (as layer (i) with a NOCC hydrated hydrogel (as layer (ii)). In such a dressing, the chitosan provides haemostatic and anti-microbial properties and the highly absorbing NOCC provides the exudate handling properties. The exclusive nature of the gel ensures that growth factors and other proteins from the wound remain in layer (i) (i.e. the chitosan layer) for ultimate delivery back to the wound. The dressing is suitable for donor sites and 2nd and 3rd degree burns. Obviously a NOCC hydrated hydrogel may be used in conjunction with other (less hydrophilic) materials as layer (i).

(2) Layer (i) may be comprised of spun hydrocolloid including a mixture of components to produce a product which is a cross between an alginate and a hydrocolloid. Thus, for example, it is possible to spin hydrocolloids from solutions of alginate, gelatin, pectin, and CMC, e.g. in the following amounts.

| Alginate | Gelatin | Pectin | CMC |
|---|---|---|---|
| 45 | 10 | 25 | 20 |
| 35 | 10 | 35 | 20 |

In this case, the layer (ii) may for example be a material as described in our aforementioned copending U.K. Patent Application No. 9415828, a relatively high sodium or potassium (e.g. 20-60%) calcium alginate, carboxymethyl cellulose or polyacrylic acid/alginate.

Layers (i) and (ii) may be joined together, e.g. by needle punching, or may be applied separately to the wound.

In a highly preferred embodiment of the invention, the dressing comprising layers (i) and (ii) is associated with a breathable film which is of increased MVTR capability in the presence of liquid water as compared to moisture vapour only. MVTR in the presence of liquid water may be measured by ASTM E96BW whereas MVTR in the presence of moisture vapour alone may be measured by ASTM E96B (water method). Preferably the value of the breathability in the presence of liquid water is at least twice and preferably at least three times that in the presence of moisture vapour alone. The value may be up to 30 or 40 times that for moisture vapour alone. Typically the film will be of a material which has an MVTR in the presence of moisture vapour alone (ASTM E96B) of 2,000 to 2,500 g m$^{-2}$ 24 hr$^{-1}$ and an MVTR in the presence of liquid water (ASTM E96BW) in the range 6.000 to 30,000 g m$^{-2}$ 24 hr$^{-1}$ (e.g. 6,00 to 10,000 g m$^{-2}$ 24 hr$^{-1}$). Typically the film will have a thickness of 30-70 microns more preferably 40-60 microns, e.g. about 50 microns.

The film may for example be of polyurethane. Suitable films are available from Innovative Technologies Limited under the designations IT325, IT425 and IT625.

An adhesive will be provided on the film for bonding the latter two the skin around the wound. The adhesive is preferably a hydroactive adhesive most preferably one which, as a continuous layer having a thickness of 20 microns, has an MVTR of 15,000 g m$^{-2}$ 24 hr$^{-1}$ using ASTM E96B. Preferably the combination of the adhesive and film is such as to provide an MVTR of 6,000 to 10.000 g m$^{-2}$ 24 hr$^{-1}$. An example of a suitable adhesive is a hydroactive adhesive available from Innovative Technologies under the designation ITHA.

The hydroactive adhesive may be provided as a continuous layer on the film. The coating thickness is preferably in the range 15 to 25 microns e.g. about 20 microns.

Alternatively the adhesive may be a pressure sensitive adhesive provided as a cross-pattern to achieve 20-50% area coverage and to achieve similar MVTRs for the combination of adhesive and film of 6,000 to 10,000 g m$^{-2}$ 24 hr$^{-1}$.

When the dressing is applied to a wound, the film will generally simply be laid over the combination of layers (i) and (ii).

In use of the dressing comprising such a film, exudate from the wound will initially be absorbed into layer (ii) and will pass therethrough until it comes into contact with the film. The breathability of the film is increased in contact with the liquid present in layer (ii), the increase being dependant on the amount of exudate present in layer (ii) (a greater amount of exudate in layer (ii) producing a greater increase in the breathability of the film). Moisture is therefore able to vent from layer (ii) via the film at a rate which is greater than the MVTR of layer (ii) which is therefore prevented from becoming saturated.

As the wound begins to dry-up during the healing process, the MVTR of the film decreases so that layer (ii) remains moist and does not dry out, thus facilitating healing.

The invention will be illustrated with reference to the following non-limiting Examples.

EXAMPLE 1

A non-woven felt made of chitosan fibres and a non-woven felt of a calcium/sodium alginate were needled together to form a two-layer dressing. The chitosan felt provides a wound contacting layer which promotes healing of the wound and also provides antimicrobial properties for the dressing. The calcium/sodium alginate felt has a high absorption capacity.

This combined dressing has the wound healing properties of the chitosan felt and the absorbency of the calcium/sodium alginate felt. By drawing the fluid away from the wound surface, the wound is kept in a relatively dry condition thereby eliminating build up of wound exudate and remove skin maceration.

EXAMPLE 2

A non-woven felt of calcium alginate fibres and a non-woven felt of a calcium/sodium alginate were needled together to form a two-layer dressing. The calcium/sodium alginate contained a minimum of 10% of sodium so as to render it more absorbent than the pure calcium alginate felt.

The calcium alginate fibre was a high M fibre which gels more easily than the high G fibre. On application to a wound, the calcium alginate fibre gels to form a moist protective layer whilst excessive fluid is taken up by the calcium/sodium alginate. The wound is therefore kept in a moist healing environment whilst maceration of healthy skin is prevented by the removal of excessive fluid to the calcium/sodium alginate fibre (the upper layer).

The invention claimed is:

1. A wound dressing comprising in combination:
   (i) a first wound contact layer of a woven, non-woven or knitted fibrous material having a level of hydrophilicity,
   (ii) a second layer of greater hydrophilicity than the first layer, and
   (iii) a breathable film having an increased MVTR capability in the presence of liquid water as compared to moisture vapour alone;
   wherein layer (i) comprises calcium alginate, zinc alginate, silver alginate, chitosan, pectin, silver N,O-carboxymethyl chitosan, or silver O-carboxymethyl chitosan.

2. A wound dressing comprising in combination:
   (i) a first wound contact layer of a woven, non-woven or knitted fibrous material having a level of hydrophilicity,
   (ii) a second layer of greater hydrophilicity than the first layer, and
   (iii) a breathable film having an increased MVTR capability in the presence of liquid water as compared to moisture vapour alone;
   wherein layer (ii) is a felt comprised of sodium alginate/calcium alginate, sodium calcium carboxymethyl cellulose, sodium zinc carboxymethyl cellulose, sodium calcium polyacrylate or sodium calcium carrageenin.

3. A wound dressing comprising in combination:
(i) a first non-woven fibrous, hydrophilic wound contact layer which comprises an alginate,
(ii) a second non-woven fibrous layer of greater hydrophilicity than the first layer applied to said first wound contact layer, and
(iii) a breathable film associated with said first wound contact layer and said second layer having an increased MVTR capability in the presence of liquid water as compared to moisture vapor alone.

4. A dressing as claimed in claim 3 wherein said layers (i) and (ii) are needle punched together.

* * * * *